United States Patent
Hedberg

(10) Patent No.: US 6,728,575 B2
(45) Date of Patent: Apr. 27, 2004

(54) METHOD AND CIRCUIT FOR DETECTING CARDIAC RHYTHM ABNORMALITIES USING A DIFFERENTIAL SIGNAL FROM A LEAD WITH A MULTI-ELECTRODE TIP

(75) Inventor: Sven-Erik Hedberg, Kungsängen (SE)

(73) Assignee: St. Jude Medical AB, Järfälla (SE)

( * ) Notice: Subject to any disclaimer, the term of this patent is extended or adjusted under 35 U.S.C. 154(b) by 326 days.

(21) Appl. No.: 09/999,131

(22) Filed: Nov. 30, 2001

(65) Prior Publication Data

US 2003/0105490 A1 Jun. 5, 2003

(51) Int. Cl.[7] ............................................. A61N 1/362
(52) U.S. Cl. ................................. 607/5; 600/518
(58) Field of Search .................. 607/4, 5, 7, 9, 607/14, 15, 17, 25, 26, 28, 122, 123, 126; 600/518, 515, 374, 375

(56) References Cited

U.S. PATENT DOCUMENTS

| | | | |
|---|---|---|---|
| 5,306,292 A | | 4/1994 | Lindegren |
| 5,324,327 A | * | 6/1994 | Cohen ........................ 607/122 |
| 5,331,966 A | * | 7/1994 | Bennett et al. ............. 600/508 |
| 5,405,373 A | * | 4/1995 | Petersson et al. ........... 607/121 |
| 5,558,097 A | * | 9/1996 | Jacobson et al. ........... 600/518 |
| 5,738,105 A | * | 4/1998 | Kroll ........................... 600/510 |
| 5,836,874 A | * | 11/1998 | Swanson et al. ............. 600/374 |
| 6,097,983 A | * | 8/2000 | Strandberg .................... 607/9 |
| 6,152,882 A | * | 11/2000 | Prutchi ........................ 600/509 |
| 6,192,273 B1 | * | 2/2001 | Igel et al. ..................... 607/14 |

* cited by examiner

Primary Examiner—Angela D. Sykes
Assistant Examiner—Joseph S Machuga
(74) Attorney, Agent, or Firm—Schiff Hardin LLP

(57) ABSTRACT

A cardiac lead has an end adapted for contact with cardiac tissue that has a number of dot-like electrodes which are separated from each other by electrically insulating material, and which are positioned at respective locations adapted for simultaneous contact with the cardiac tissue. The dot-like electrodes produce respective unipolar signals. At least one difference signal from the unipolar signals of a pair of the dot-like electrodes. The difference signal is edited in circuitry of a cardiac assist device and is compared to a threshold. If the threshold is exceeded, a signal indicating a cardiac rhythm abnormality, such as fibrillation, is generated for triggering electrical therapy delivered to the cardiac tissue by the cardiac assist device.

26 Claims, 5 Drawing Sheets

METHOD AND CIRCUIT FOR DETECTING CARDIAC RHYTHM ABNORMALITIES USING A DIFFERENTIAL SIGNAL FROM A LEAD WITH A MULTI-ELECTRODE TIP

BACKGROUND OF THE INVENTION

1. Field of the Invention

The present invention is directed to a method and circuit suitable for use in pacemakers, cardioverters, defibrillators, and the like, making use of a lead having a tip with multiple electrodes to detect cardiac rhythm abnormalities, such as fibrillation and tachycardia.

2. Description of the Prior Art

A cardiac lead typically has a proximal end with a connector adapted for electrical and mechanical connection to a cardiac-assist device, such as a pacemaker, cardioverter or defibrillator, and an opposite distal end, at which one or more electrodes is/are located. Between the distal end and the proximal end, the lead has a flexible insulating sheath or jacket, containing conductors depending on the number of electrodes.

The electrodes are exposed conductive surfaces at the distal end of the lead. Conventional electrode configurations include a unipolar configuration and a bipolar configuration. In a unipolar configuration, there is only one electrode at the distal end, typically a hemisphere covering the distal tip. Typically the housing, or a portion thereof, of the cardiac assist device is used as the indifferent or return electrode. A bipolar lead has two electrode surfaces, separated from each other by a spacing. Typically one of these electrodes is formed as a hemispherical electrode at the distal tip of the lead, and the other is a ring electrode, which annularly surrounds the sheath, located a short distance behind the tip electrode.

In most modern cardiac assist devices, the electrode lead is not only used to deliver an appropriate cardiac assist regimen in the form of electrical pulses, but also is used to detect cardiac activity. The detection of cardiac activity can serve many purposes, such as for use in determining whether adjustments to the cardiac assist regimen are necessary, as well as for identifying cardiac rhythm abnormalities which may require immediate preventative action, such as the occurrence of tachycardia or fibrillation. Particularly in the case of a cardioverter or a defibrillator, which is normally passive unless and until tachycardia or fibrillation is detected, it is important not only to reliably detect tachycardia or fibrillation when they occur, but also it is important not to misidentify a non-emergency cardiac rhythm abnormality as tachycardia or fibrillation, since administering the emergency regimen to a healthy heart can possibly create an emergency situation where none exists. Moreover, at least in the case of a defibrillator, unnecessary triggering of the extremely strong defibrillation energy will cause considerable discomfort to the patient.

An electrode lead for a cardiac pacemaker is disclosed in U.S. Pat. No. 5,306,292 which has a distal tip with a number of closely spaced electrodes thereon, with the remainder of the hemispherical surface of the distal tip of the electrode being non-conducting. Circuitry in the pacemaker housing, connected to the respective electrodes via the electrode lead cable, allows the total conductive area and geometry of the distal tip of the electrode lead to be selectively varied, by activating the electrodes in different combinations. For example, the combination of electrodes (i.e. conductive surfaces) at the electrode tip which provides the lowest stimulation threshold can be determined by an autocapture unit, so that energy consumption can be reduced.

Many algorithms are known for analyzing the detected signal wave forms obtained with unipolar and bipolar leads. A prerequisite to the proper functioning of most of these algorithms is that the signal which enters into the algorithm be relatively noise-free. The detected signal, in its raw form, can be corrupted by noise produced by electromagnetic interference in the patient's environment, as well as by muscle activity. Such noise may mimic a fibrillation pattern, for example, particularly in the case of a unipolar lead, but also to a certain extent with a bipolar lead.

Conventional noise-removing techniques involve filtering and other types of signal editing procedures.

After making the incoming signal reasonably noise-free, conventional detection algorithms analyze the signal by undertaking one or more threshold comparisons and/or by analyzing the rate of occurrence of a particular characteristic of the signal (i.e., maxima, minima, zero crossings, etc.) over a given period of time. Comparison of the signal waveform to stored signal templates, respectively representing previously-obtained abnormal signals, is also a known technique. In this manner, a determination is made as to whether the incoming signal represents normal sinus rhythm, a PVC, tachycardia, atrial fibrillation, ventricular fibrillation, etc.

SUMMARY OF THE INVENTION

It is an object of the present invention to provide a method and a circuit for analyzing signals obtained with such a cardiac lead for the purpose of detecting cardiac abnormalities so that remedial action can be taken.

The above object is achieved in accordance with the principles of the present invention in a method and circuit for use with a cardiac lead having multiple electrodes or conductive surfaces ("dots") at its distal tip, wherein each dot has its own conductor in the lead, in which a unipolar signal from that dot is conducted. A differential signal is obtained between the respective unipolar signals for two such dots. It has been found that the respective unipolar signals of a lead with electrodes (conductive surfaces) very close to each other, on the order of a few tenths of a millimeter of separation, exhibit morphologic differences to a greater extent during fibrillation than during normal heart activity. This morphologic difference is exploited in the method and circuit of the present invention, wherein appropriate editing of the differential signal is undertaken to detect these morphologic differences. In the method and circuit of the invention, the differential signal is supplied to a bandpass filter, which can be formed from a low-pass filter having a corner frequency of approximately 10 Hz followed by a 5 Hz high-pass filter. The signal from this bandpass filter is then rectified and then supplied to a low-pass filter, preferably a 0.5 Hz low-pass filter. The output from this low-pass filter is supplied to a threshold detector. Signals above the threshold of the threshold detector represent detection of a signal representing cardiac abnormality. Signals above the threshold with this type of signal editing have been found to occur when a state of fibrillation exists. By similarly analyzing a number of differential signals respectively obtained from different pairs of electrode dots, the reliability of the fibrillation detection can be enhanced even further. Preferably, a lead having a tip with two to seven dots is employed.

The dot-like electrodes of the lead used with the inventive method and circuit are individually formed of conductive material, and are separated at the surface of the distal tip of the electrode by electrically insulating material. The arrangement of the electrode dots can include a centrally disposed electrode dot, with a number of further of electrode dots annularly arranged around the centrally disposed dot. The annularly arranged electrode dots can be located at radially symmetrical positions relative to the centrally disposed dot.

A very small distance between two dots results in the cardiac differential signal detected by a pair of dots having a slightly reduced amplitude in comparison to the signal detected by a conventional unipolar or bipolar lead, however, the signal detected by each electrode dot pair already has a significantly reduced noise content in comparison to conventionally obtained signals, so that much less editing in order to remove noise artifacts from the signals is necessary.

Each electrode dot preferably has a diameter of 0.5 mm, with the edge-to-edge distances among all of the respective dots being approximately equal.

In accordance with the invention, one appropriate method for analyzing the signals obtained from the respective electrode dots is to obtain unipolar signals from the respective dots with the cardiac assist housing serving as the ground level. By producing a difference signal between respective signals from two dots, a bipolar differential signal is obtained, although this will be different from a conventional bipolar signal obtained with a tip electrode and a ring electrode configuration. Multiple difference signals are thus available for analysis. It is also possible to employ one of the electrode dots as a ground reference, and to refer all of the difference signals to the signal obtained from that one dot.

DESCRIPTION OF THE PREFERRED EMBODIMENTS

Figure 1:
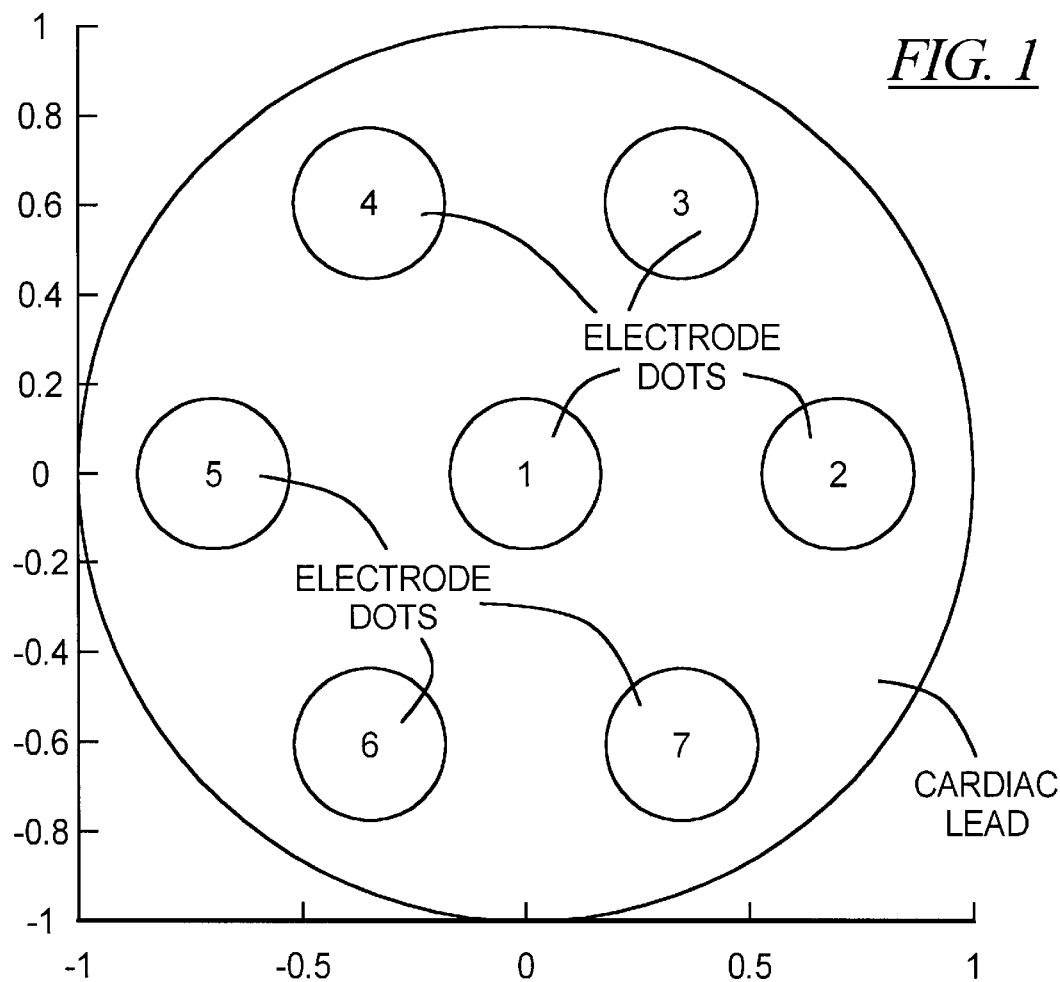
FIG. 1 is a schematic end view of the tip of an electrode lead, in an embodiment having seven electrode dots, for use in accordance with the principles of the present invention.

An embodiment of an electrode lead constructed in accordance with the principles of the present invention is shown in FIG. 1, which is a view looking directly at the distal tip (greatly enlarged) of the electrode lead. As can be seen in FIG. 1, the electrode tip has a number of electrode dots distributed thereon, including a centrally disposed electrode dot 1 and a number of other electrode dots arranged relative to the centrally disposed electrode dot 1. In the embodiment of FIG. 1, six other electrode dots 2–7 are shown, for a total of seven electrode dots in the embodiment of FIG. 1. In the embodiment of FIG. 1, the electrode dots 2–7 are shown as being annularly arranged around the centrally disposed electrode dot 1, however, other locations are possible. The only constraint is that the dot-to-dot spacing between each electrode dot and its neighbors should be approximately the same.

The axes shown in FIG. 1 are in arbitrary units and are solely for the purpose of providing a guide as to the relative placement of the electrode dots 1–7. Each electrode dot will have a diameter of approximately 0.5 mm.

The electrode tip shown in FIG. 1 is at the distal end of a flexible, implantable electrode lead, having an opposite end with a plug adapted to be fitted into a cardiac assist device, such as a pacemaker, cardioverter or defibrillator. The lead will contain respective conductors for the electrode dots 1–7, each conductor being insulated from the others and the entire lead being jacketed in an insulating sheath, as is standard. The surface of the electrode tip surrounding the respective electrode dots 1–7 is composed of insulating material, so that the electrode dots are electrically insulated from each other.

In practice, a unipolar signal is obtained from each of the electrode dots 1–7, i.e., seven unipolar signals are obtained. These unipolar signals can be analyzed by forming a differential signal between the respective unipolar signals from any two of the electrode dots. The differential signal obtained in accordance with the invention is not the same as a signal obtained using a conventional bipolar lead with a tip electrode and a ring electrode. The dissimilarity is due to the differences in geometry between the lead shown in FIG. 1 and a conventional bipolar lead.

Figure 2:
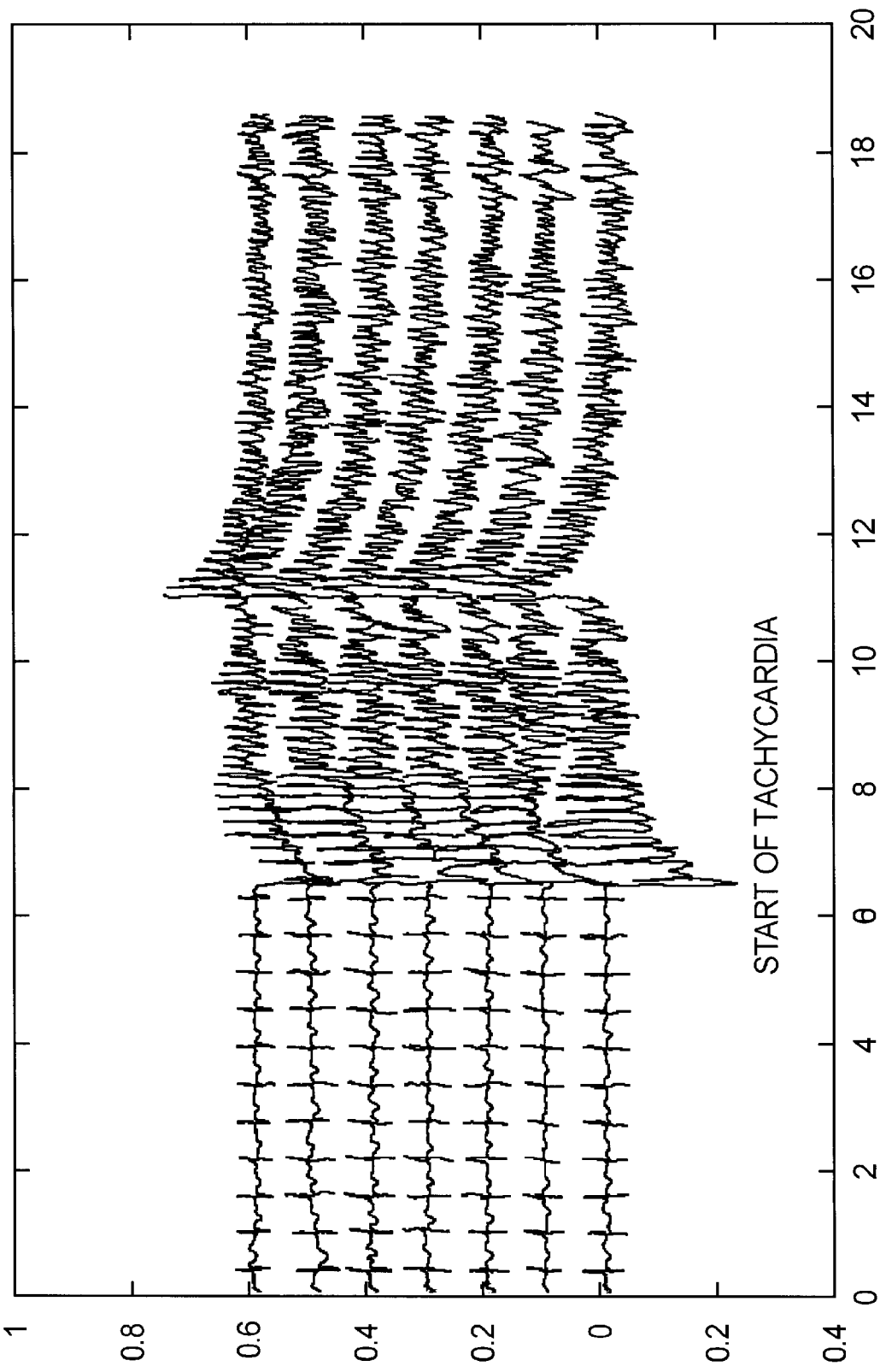
FIG. 2 shows the respective signals from the electrode dots in the embodiment of FIG. 1 in a unipolar mode showing normal sinus rhythm, followed by tachycardia, followed by fibrillation.
Figure 3:
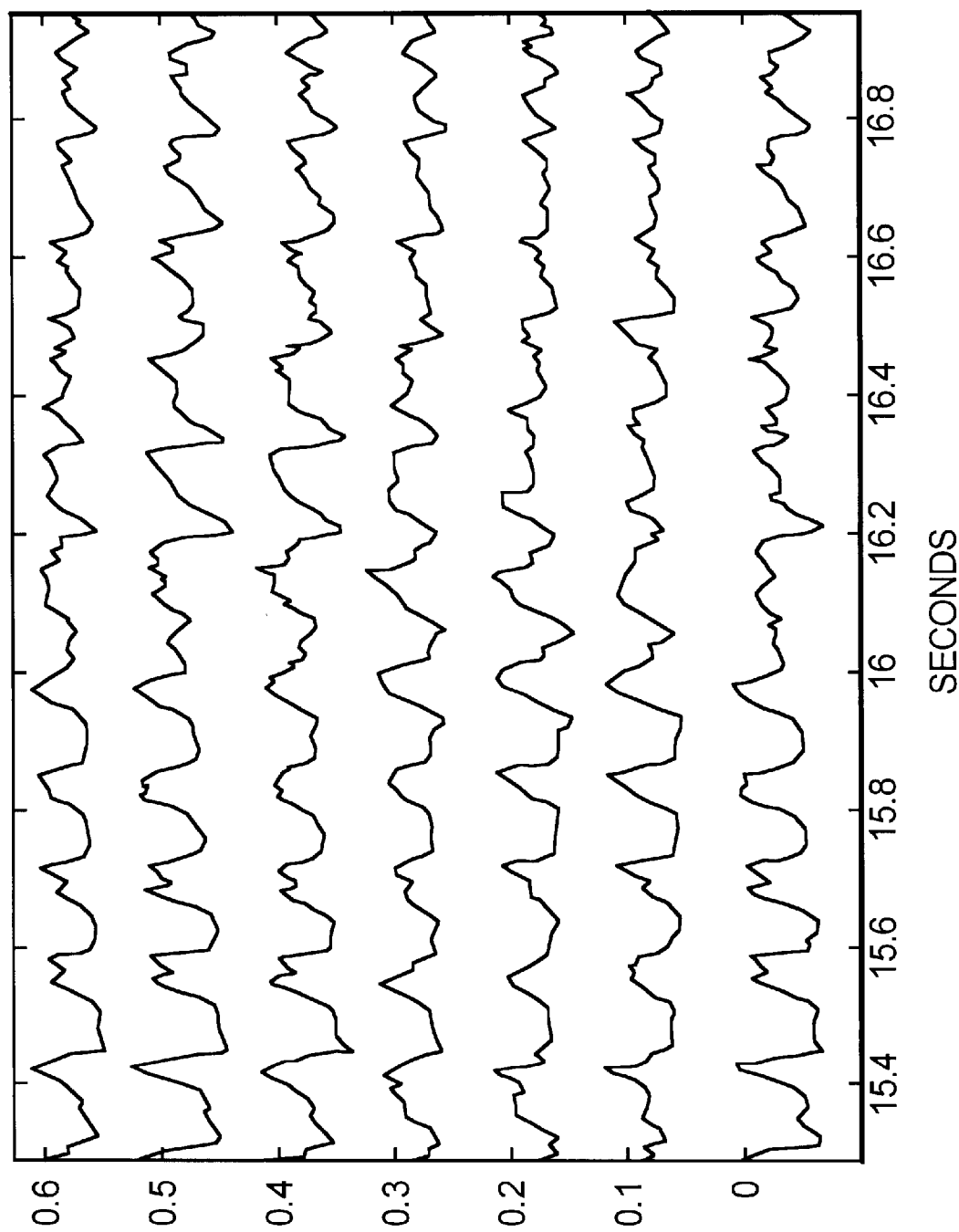
FIG. 3 shows the respective signals from the electrode dots in the embodiment of FIG. 1 several seconds into the fibrillation shown in FIG. 2.

FIG. 2 shows an example of the respective unipolar signals received from the electrode dots 1–7 in the embodiment of FIG. 1. Normal sinus rhythm is shown at the left of the drawing, and it can be seen that tachycardia begins shortly after six seconds, followed by fibrillation at approximately eleven seconds. FIG. 3 shows the respective signals several seconds into the fibrillation.

Figure 4:
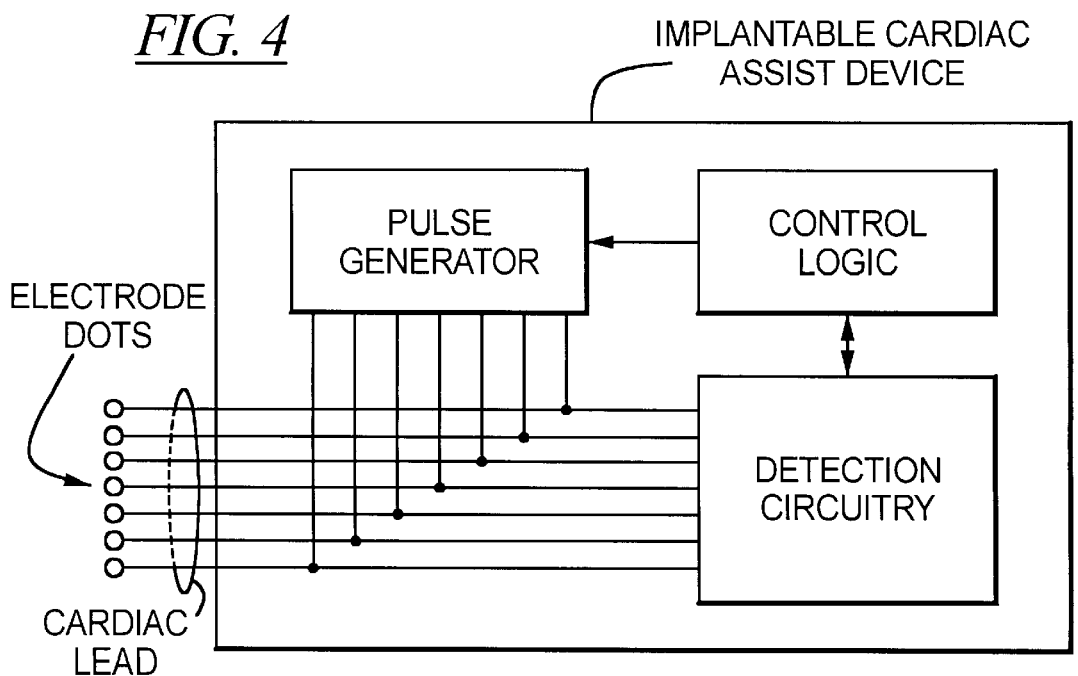
FIG. 4 is a block diagram showing the basic components of an implantable cardiac assist device, constructed and operating in accordance with the principles of the present invention.

The basic components of an implantable cardiac assist device in accordance with the invention are shown in FIG. 4. The implantable cardiac assist device can be a pacemaker, a cardioverter or a defibrillator, for example.

The implantable cardiac assist device shown in FIG. 4 has a cardiac lead with a cardiac tip having electrode dots thereon, such as shown in FIG. 1. Each electrode dot has its own conductor in the cardiac lead. These conductors are connected to detection circuitry in the implantable cardiac assist device. The detection circuitry is connected to control logic which, among other things, controls a pulse generator, also connected to the respective dot conductors. The control logic controls the pulse generator to supply stimulation pulses via the cardiac lead conductors and the electrode dots, to cardiac tissue according to any of the number of known therapy modes. When pulses are being delivered via the conductors, the detection circuitry can be inhibited by the control logic in a known manner.

The pulse generator in FIG. 4 is intended to generically represent any type of generator for delivering therapy in the form of electrical stimulation to cardiac tissue, and thus represents one or more of a pacing pulse generator, a cardioversion pulse generator, and/or a defibrillation pulse generator. If the implantable cardiac assist device performs the functions of a pacemaker, the detection circuitry, in addition to the inventive circuitry described herein, will include, or be augmented by, all of the conventional pacing detection circuitry and the pulse generator will be operated to generate pacing pulses in a conventional manner. Upon the detection of a cardiac rhythm abnormality, such as defibrillation, by the inventive detection circuitry, the control logic will be informed of the occurrence of fibrillation, and it will operate the pulse generator to deliver appropriate defibrillation pulses. All combinations of pacing stimulation and pacing detection, cardioversion stimulation and cardioversion detection and defibrillation stimulation and fibrillation detection can be employed.

In addition to the basic component shown in FIG. 4, the implantable cardiac assist device will include all other standard components such as a battery, telemetry circuitry, etc. which are all well-known to those of ordinary skill in the art and need not be specifically described herein.

Detection circuitry operating according to the procedure described above is shown in FIG. 5, wherein unipolar signals from electrode dots 2 and 5 are used, as an example. The difference between these unipolar signals is formed and supplied to a bandpass filter formed by a low-pass filter and a high-pass filter. The low-pass filter preferably has a 10 Hz corner frequency, and the high-pass filter is preferably a 5 Hz high-pass filter. The output of the bandpass filter is then rectified in an absolute value former. The output of the absolute value former, as a rectified signal is supplied to another low-pass filter. This further low-pass filter is preferably a 0.5 Hz low-pass filter. The output of the further low-pass filter is supplied to a level (threshold) detector. The output of this level detector is used as the signal indicating detection of fibrillation (if it exists), and is supplied to the control logic. Only the output of the second low-pass filter is supplied to the level detector. In an experimental setup, the output of the absolute value former and the inputs from the electrode dots 2 and 5 were supplied to an oscilloscope for display, together with the output of the second low-pass filter. The waveforms of these respective signals are shown in FIG. 6.

Figure 5:
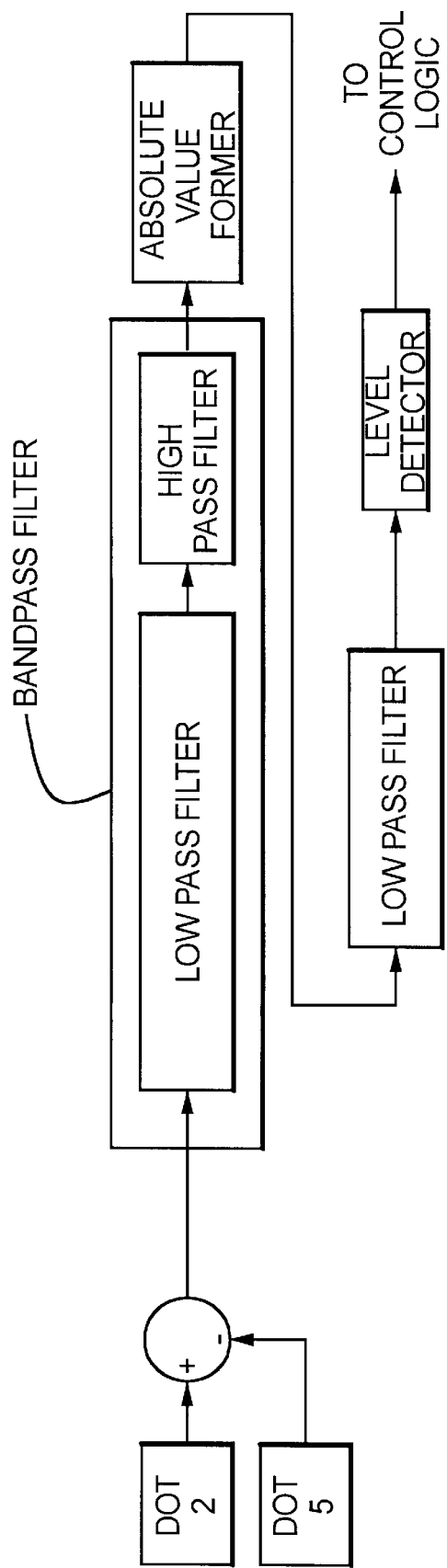
FIG. 5 is a block diagram of a difference circuit for analyzing signals from two of the electrode dots in accordance with the principles of the present invention.
Figure 6:
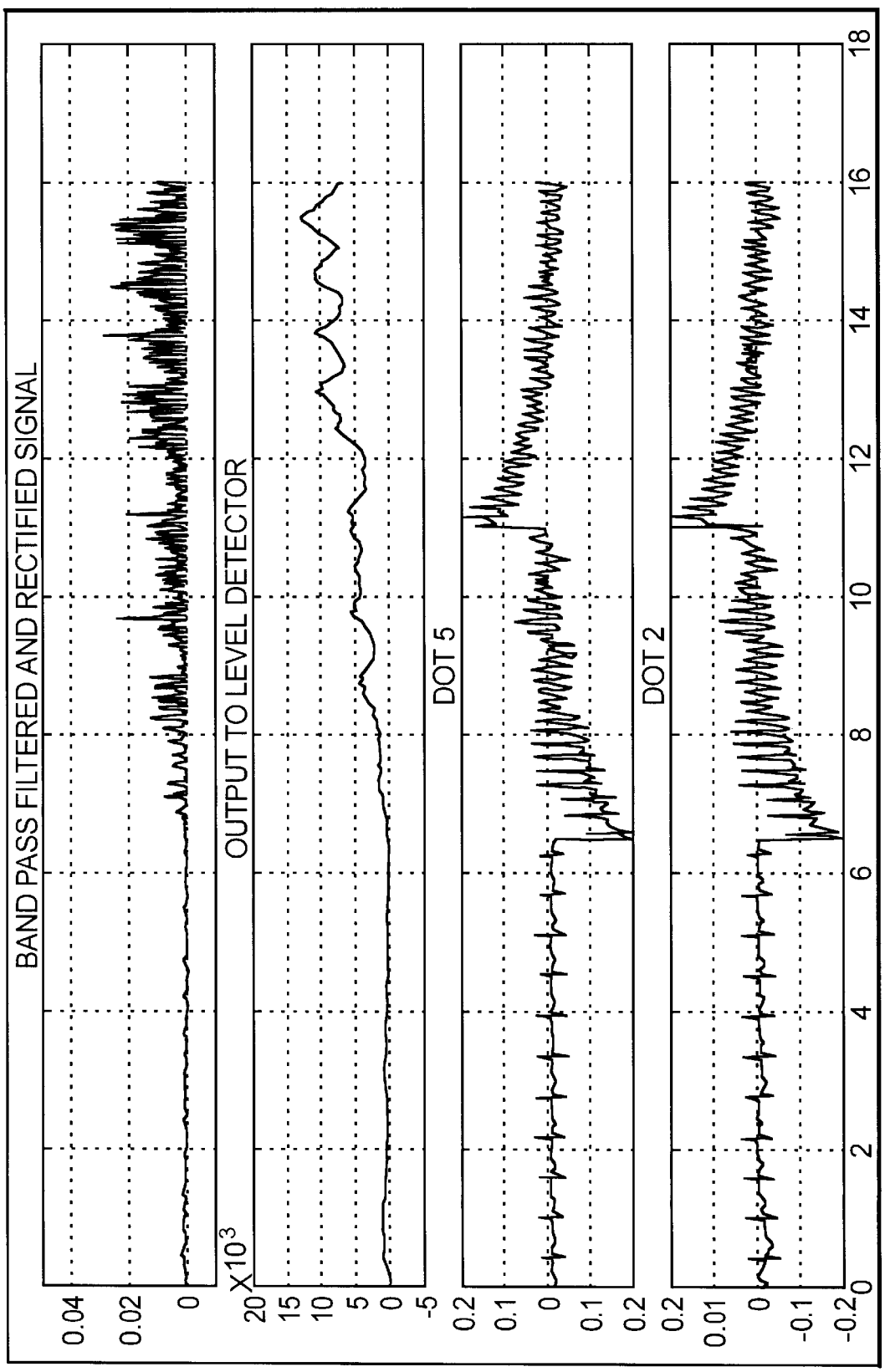
FIG. 6 illustrates signals at respective locations in the block diagram of FIG. 5.

Multiple versions of the detector shown in FIG. 5 can be used for different pairs of electrode dots, with the level detector output for the pair producing the highest output being used as the indicator for the occurrence of fibrillation.

As can be seen by observing the respective signals from the electrode dots at the left side of FIG. 2, as occur during normal sinus rhythm, these respective signals are highly uniform and vary only insignificantly from dot-to-dot. This is contrasted with the situation several seconds into fibrillation shown in FIG. 3, wherein it can be observed that even though the respective signals exhibit gross similarities, the respective morphologies of the signals are sufficiently different so that a difference signal, formed between any two of the dots, will have a non-zero value. Moreover, this difference signal will be relatively noise-free, at least compared to a conventional bipolar signal as occurs during fibrillation. The relatively low noise level in the difference signal formed from pairs of dot electrode signals, compared to a signal from a conventional bipolar lead, is due to the relative width of the propagating wave front in comparison to the distance between the electrodes, in the two situations. The width of the wave front is about 1.5 mm, which is much shorter than the conventional tip-ring distance of a conventional bipolar lead, which is approximately 12 mm. For a conventional tip-ring bipolar lead, therefore, the entire wave front virtually completely passes one electrode before it reaches the other (although there are exceptions if the wave front happens to be traveling in a direction perpendicular to a line between the two electrodes).

In the case of a lead having a tip with electrode dots as described herein, the inter-electrode distance, as described above, is less than or on the order of the wave front width. During normal cardiac activity, the unipolar signals from each dot are more or less equal in their low-frequency (below 50 Hz) components. Upon an onset of fibrillation, a more disorganized cell activity occurs. The similarity of the unipolar signals from each dot will decrease, and the difference signals from dot pairs therefore will be different in the case of fibrillation, compared to normal sinus activity.

By analyzing the individual unipolar signals obtained from the respective dots, it has been determined that bandpass filtering those signals, with a bandpass filter which includes a low-pass filter having a corner frequency of 10 Hz enhances the fibrillation signals more than signals from normal sinus activity. The high-pass filter easily filters out any baseline variations.

If the electrode lead tip has more than two dots, as is preferred, more than one detector of the type described in connection with FIG. 5 can be used, and the electrode dot pair which produces the highest output can then be selected as the signal used for fibrillation detection.

Upon emission of a signal from the level detector to the control logic indicating the presence of fibrillation, the control logic operates the pulse generator to initiate appropriate defibrillation therapy, in a known manner.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for detecting fibrillation comprising the steps of:
    providing a plurality of separated dot-like electrodes at an end of a cardiac lead and placing said plurality of dot-like electrodes in simultaneous contact with cardiac tissue;
    detecting cardiac activity via said dot-like electrodes and generating respective unipolar signals, representing said cardiac activity, from said plurality of dot-like electrodes;
    forming a difference signal from the respective unipolar signals from a pair of said dot-like electrodes;
    bandpass filtering said difference signal to obtain a bandpass filtered signal;
    rectifying said bandpass filtered signal to obtain a rectified signal;
    low-pass filtering said rectified signal to obtain a low-pass filtered signal; and
    comparing said low-pass filtered signal to a threshold and, if said low-pass filtered signal exceeds said threshold, generating a signal indicating an occurrence of fibrillation.

2. A method as claimed in claim 1 comprising forming a bandpass filter from a low-pass filter followed by a high-pass filter, and bandpass filtering said difference signal in said bandpass filter.

3. A method as claimed in claim 2 comprising employing a low-pass filter having a corner frequency of approximately 10 Hz as said low-pass filter in said bandpass filter.

4. A method as claimed in claim 2 comprising employing a 5 Hz high-pass filter as said high-pass filter in said bandpass filter.

5. A method as claimed in claim 1 comprising forming a bandpass filter from a low-pass filter having a corner frequency of approximately 10 Hz followed by a 5 Hz high-pass filter, and bandpass filtering said difference signal in said bandpass filter.

6. A method as claimed in claim 1 comprising low-pass filtering said rectified signal in a 0.5 Hz low-pass filter.

7. A method as claimed in claim 1 comprising forming a band pass filter from a low-pass filter having a corner frequency of approximately 10 Hz followed by a 5 Hz high-pass filter and band pass filtering said difference signal in said bandpass filter, and rectifying said bandpass filtered signal to obtain a rectified signal prior to low-pass filtering said rectified signal in a 0.5 Hz low-pass filter.

8. A method as claimed in claim 1 wherein the step of providing a plurality of separated dot-like electrodes at an end of a cardiac lead comprises providing a plurality in a range of two to seven separated dot-like electrodes at said end of said cardiac lead.

9. A method as claimed in claim 1 wherein the step of forming a difference signal comprises forming a plurality of difference signals respectively from the respective unipolar signals from a plurality of pairs of said dot-like electrodes, and wherein the step of bandpass filtering said difference signal comprises bandpass filtering each of said difference signals to obtain a plurality of bandpass filtered signals, and wherein the step of rectifying said bandpass filtered signal comprises rectifying each of said bandpass filtered signals to obtain a plurality of rectified signals, and wherein the step of low-pass filtering said rectified signal comprises low-pass filtering said plurality of rectified signals to obtain a plurality of low-pass filtered signals, and wherein the step of comparing said low-pass filtered signal to a threshold comprises comparing a low-pass filtered signal, among said plurality of low-pass filtered signals, having a highest amplitude to said threshold.

10. A fibrillation detector comprising:

a cardiac lead having a plurality of separated dot-like electrodes at an end of said cardiac lead and said plurality of dot-like electrodes being adapted for placement in simultaneous contact with cardiac tissue, said dot-like electrodes generating respective unipolar signals, representing said cardiac activity;

a difference former connected to said cardiac lead which forms a difference signal from the respective unipolar signals from a pair of said dot-like electrodes;

a bandpass filter in which said difference signal is filtered to obtain a bandpass filtered signal;

a rectifier in which said bandpass filtered signal is rectified to obtain a rectified signal;

a low-pass filter in which said rectified signal is low-pass filtered to obtain a low-pass filtered signal; and a comparator which compares said low-pass filtered signal to a threshold and which, if said low-pas filtered signal exceeds said threshold, generates a signal indicating an occurrence of fibrillation.

11. A fibrillation detector as claimed in claim 10 wherein said bandpass filter comprises a low-pass filter followed by a high-pass filter.

12. A fibrillation detector as claimed in claim 11 wherein said low-pass filter in said bandpass filter has a corner frequency of approximately 10 Hz.

13. A fibrillation detector as claimed in claim 11 wherein said high-pass filter is a 5 Hz high-pass filter.

14. A fibrillation detector as claimed in claim 10 wherein said bandpass filter comprises a low-pass filter having a corner frequency of approximately 10 Hz followed by a 5 Hz high-pass filter.

15. A fibrillation detector as claimed in claim 10 wherein said low-pass filter is a 0.5 Hz low-pass filter.

16. A fibrillation detector as claimed in claim 10 wherein said bandpass filter comprises a low-pass filter having a corner frequency of approximately 10 Hz followed by a 5 Hz high-pass filter, and wherein said low-pass filter which low-pass filters said rectified signal is a 0.5 Hz low-pass filter.

17. A fibrillation detector as claimed in claim 10 wherein said cardiac lead has a plurality of two to seven separated dot-like electrodes at said end of said cardiac lead.

18. A defibrillator comprising:

a cardiac lead having a plurality of separated dot-like electrodes at an end of said cardiac lead and said plurality of dot-like electrodes being adapted for placement in simultaneous contact with cardiac tissue, said dot-like electrodes generating respective unipolar signals, representing said cardiac activity;

a pulse generator, connected to said cardiac lead, which emits a defibrillation pulse;

a fibrillation detector comprising a difference former connected to said cardiac lead which forms a difference signal from the respective unipolar signals from a pair of said dot-like electrodes, a bandpass filter in which said difference signal is filtered to obtain a bandpass filtered signal, a rectifier in which said bandpass filtered signal is rectified to obtain a rectified signal, a low-pass filter in which said rectified signal is low-pass filtered to obtain a low-pass filtered signal, and a comparator which compares said low-pass filtered signal to a threshold and which, if said low-pass filtered signal exceeds said threshold, generates a signal indicating an occurrence of fibrillation; and a control unit connected to said fibrillation detector and to said pulse generator for controlling said pulse generator to emit said defibrillation pulse upon receiving said signal indicating an occurrence of fibrillation from said fibrillation detector.

19. A defibrillator as claimed in claim 18 wherein said bandpass filter comprises a low-pass filter followed by a high-pass filter.

20. A defibrillator as claimed in claim 19 wherein said low-pass filter in said bandpass filter has a corner frequency of approximately 10 Hz.

21. A defibrillator as claimed in claim 19 wherein said high-pass filter is a 5 Hz high-pass filter.

22. A defibrillator as claimed in claim 19 wherein said bandpass filter comprises a low-pass filter having a corner frequency of approximately 10 Hz followed by a 5 Hz high-pass filter.

23. A defibrillator as claimed in claim 18 wherein said low-pass filter is a 0.5 Hz low-pass filter.

24. A defibrillator as claimed in claim 18 wherein said bandpass filter comprises a low-pass filter having a corner frequency of approximately 10 Hz followed by a 5 Hz high-pass filter, and wherein said low-pass filter which low-pass filters said rectified signal is a 0.5 Hz low-pass filter.

25. A defibrillator as claimed in claim 18 wherein said cardiac lead has a plurality of two to seven separated dot-like electrodes at said end of said cardiac lead.

26. A defibrillator as claimed in claim 18 wherein said difference former forms a plurality of difference signals respectively from the respective unipolar signals from a plurality of pairs of said dot-like electrodes, and wherein said bandpass filter filters said plurality of difference signals to obtain a plurality of bandpass filtered signals, and wherein said rectifier rectifies said plurality of bandpass filtered signals to obtain a plurality of rectified signals, and wherein said low-pass filter filters said plurality of rectified signals to obtain a plurality of low-pass filtered signals, and wherein said comparator compares a low-pass filtered signal, among said plurality of low-pass filtered signals, having a highest amplitude to said threshold and, if said low-pass filtered signal having said highest amplitude exceeds said threshold, generates said signal indicating an occurrence of fibrillation.

* * * * *